United States Patent [19]

Smits

[11] Patent Number: 5,049,775
[45] Date of Patent: Sep. 17, 1991

[54] INTEGRATED MICROMECHANICAL PIEZOELECTRIC MOTOR

[75] Inventor: Johannes G. Smits, Quincy, Mass.

[73] Assignee: Boston University, Boston, Mass.

[21] Appl. No.: 251,565

[22] Filed: Sep. 30, 1988

[51] Int. Cl.$^5$ .......................................... H01L 41/08
[52] U.S. Cl. ................................. 310/328; 310/331; 310/332
[58] Field of Search .............................. 310/330–332, 310/322–324, 328

[56] References Cited

U.S. PATENT DOCUMENTS

| | | | |
|---|---|---|---|
| 2,842,685 | 7/1958 | Petermann et al. | 310/331 X |
| 3,146,367 | 8/1964 | McNaney | 310/331 X |
| 3,490,771 | 1/1970 | Bauer | 310/330 X |
| 3,928,778 | 10/1975 | Ivanov et al. | 310/331 |
| 4,233,637 | 11/1980 | Kubota | 310/331 X |
| 4,399,386 | 8/1983 | Osaka et al. | 310/331 X |
| 4,453,103 | 6/1984 | Vishnevsky et al. | 310/328 X |
| 4,453,755 | 8/1984 | O'Neill | 310/328 X |
| 4,489,609 | 12/1984 | Burdess et al. | 310/333 X |
| 4,517,486 | 5/1985 | Andrews | 310/331 |
| 4,523,120 | 6/1985 | Assard et al. | 310/331 X |
| 4,565,940 | 1/1986 | Hubbard, Jr. | 310/326 |
| 4,610,475 | 9/1986 | Heiserman | 310/332 X |
| 4,613,782 | 9/1986 | Mori et al. | 310/328 X |
| 4,622,483 | 11/1986 | Staufenberg, Jr. et al. | 310/328 |
| 4,626,730 | 12/1986 | Hubbard, Jr. | 310/326 |
| 4,667,997 | 5/1987 | Udagawa et al. | 310/332 X |
| 4,686,440 | 8/1987 | Hatamura et al. | 310/331 X |
| 4,714,855 | 12/1987 | Fujimoto | 310/328 |
| 4,719,383 | 1/1988 | Wang et al. | 310/324 |
| 4,727,278 | 2/1988 | Staufenberg, Jr. et al. | 310/328 |
| 4,740,410 | 4/1988 | Muller et al. | 428/133 |
| 4,742,260 | 5/1988 | Shimizu et al. | 310/331 X |
| 4,764,244 | 8/1988 | Chitty et al. | 310/321 X |
| 4,776,924 | 10/1988 | Delapierre | 310/330 X |
| 4,857,791 | 8/1989 | Uchino | 310/328 X |
| 4,890,370 | 1/1990 | Fukuda et al. | 310/320 X |
| 4,906,840 | 3/1990 | Zdeblick et al. | 310/328 X |

FOREIGN PATENT DOCUMENTS

| | | | |
|---|---|---|---|
| 0143128 | 7/1980 | Fed. Rep. of Germany | 310/331 |
| 0143682 | 9/1980 | Fed. Rep. of Germany | 310/323 |
| 0093477 | 6/1983 | Japan | 310/323 |
| 0060482 | 3/1984 | Japan | 310/328 |
| 60-72277 | 4/1985 | Japan | |
| 0022779 | 1/1986 | Japan | 310/323 |
| 0185079 | 8/1986 | Japan | 310/331 |
| 0058883 | 3/1987 | Japan | 310/328 |
| 0081984 | 4/1987 | Japan | 310/323 |
| WO89/07256 | 8/1989 | PCT Int'l Appl. | |
| 2168481 | 6/1986 | United Kingdom | 310/330 |
| WO88/05314 | 7/1988 | World Int. Prop. O. | |

OTHER PUBLICATIONS

Novel Three-Dimensional Positioner & Scanner for the STM Using Shear Deformation of Piezoelectric Plates; by K. Vozumi et al., published article Dec. 14, 1987; pp. L123-L126.

*J. Phys. D: Appl. Phys.*; vol. 11, 1978; Steel et al., pp. 979-989.

*Panasonic Technical Reference*; "Ultrasonic Motor"; pp. 1-10.

*Design News*; "Piezoelectric Actuators Generate Many Motion Patterns"; 1987.

*Micro Pulse Systems*; Jul. 1986, "A New Technology In Micropositioning Instruments"; 5 pages.

Literature from Piezo Electric Products, Inc.; Cambridge, MA.

Reprint from *Japanese Journal of Applied Physics*; vol. 22, No. 12; Dec. 1983; "Micro-Angle Adjusting Device Using PMN Electrostrictors"; Aizawa et al.; pp. 1925-1927.

Literature from Microflex Technology, Inc.; Columbus, Ohio.

*Primary Examiner*—Mark O. Budd
*Attorney, Agent, or Firm*—Hamilton, Brook, Smith & Reynolds

[57] ABSTRACT

Small piezoelectric machines comprised of pairs of cantilever beams covered with a piezoelectric material are driven to perform various mechanical tasks. A robot utilizes a plurality of pairs of these piezoelectrically driven beams to move itself and grab, carry or manipulate other objects.

36 Claims, 11 Drawing Sheets

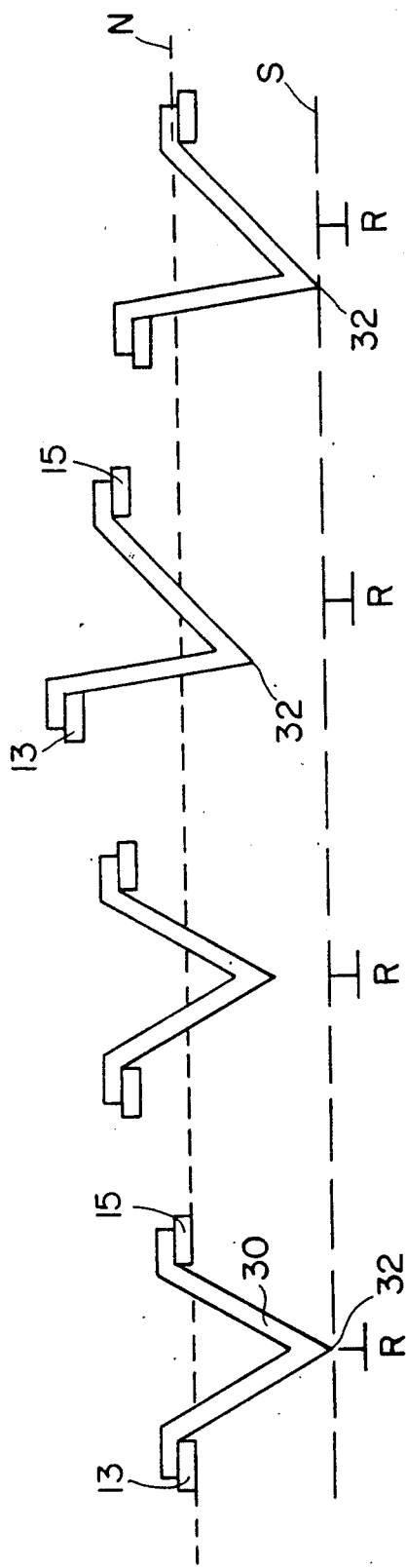

INTEGRATED MICROMECHANICAL PIEZOELECTRIC MOTOR

BACKGROUND OF THE INVENTION

The present invention relates generally to the field of piezoelectrically driven elements, and in particular, to piezoelectric micromachines used to perform precise tasks or functions.

Certain ceramics, organic polymers and inorganic crystals are known to expand or contract when they are positioned within an electric field at a rate directly proportioned to said electric field. These "piezoelectric" materials will contract or expand depending on the polarity of the applied field. Conversely these materials will also transform a mechanical force into an electrical signal. Thus, if an alternating voltage is applied, periodic variations in the geometry of the material will occur.

When a film of piezoelectric material is secured to a surface of a flexible beam or membrane of appropriate dimension to form a "bimorph" structure, the free portion of the beam or membrane can be made to deflect in a precise and predetermined manner in a direction perpendicular to the plane of the structure. These piezoelectric bimorph structures have been used to perform various functions including operation as transducers, pumps and shutters. Piezoelectric motors, fans and actuators have also been constructed that perform certain types of mechanical functions. The motors utilize piezoelectric driving elements to rotate or translate driven members.

SUMMARY OF THE INVENTION

The present invention is comprised of a piezoelectric micromachine that uses fabricated pairs of cantilever beams partially covered with a piezoelectric material so that the beams can be electrically driven to perform various kinds of mechanical tasks. The beams or piezoelectrically driven members are formed from a semiconductor material using microfabrication techniques employed in the manufacture of semiconductor devices.

A preferred embodiment utilizes silicon beams extending from a silicon frame that have all been etched from a silicon wafer. A surface of each beam is covered with a piezoelectric material through which an electric field is passed to cause the piezoelectric film to either expand or contract depending upon the polarity of the applied field. This expansion or contraction results in the bending of the beam to which it is attached. The bending of the beams adjacent to each other can be used to perform tasks requiring small and precise manipulation of objects.

By connecting a single flexible "V" shaped member or "foot" between the free ends of each beam a walking motion can be effected by the appropriate displacement of the two beams relative to each other. If two or more of these machines are operated together in a controlled sequence, a small robot can be constructed that can move or walk from one location to another and grab, carry and manipulate objects. For example, the robot can be fitted with piezoelectric tweezers or jaws to grasp and carry objects, or alternatively, a cutting tool for applications requiring precise cutting.

Such a robot can be powered by a solar cell mounted on the main body. A central microprocessor with a programmable memory can be used to control and coordinate the "legs" of the robot. This permits the robot to be programmed to perform predefined tasks. The robot can also be fitted with acoustic sensors or some other transducer that can be used to program the memory or directly control robot operation. Numerous other functions can be performed by these machines such as the driving of a wheel.

The above, and other features of the invention including various novel details of construction and combination of parts, will now be more particularly described with reference to the accompanying drawings and pointed out in the claims. It will be understood that the particular piezoelectric micromachine embodying the invention is shown by way of illustration only and not as a limitation of the invention. The principle features of this invention may be employed in various embodiments without departing from the scope of the invention.

BRIEF DESCRIPTION OF THE DRAWINGS

FIGS. 2a–2d illustrate a sequence of positions that the machine can assume that result in a walking motion.

DETAILED DESCRIPTION

Figure 1:
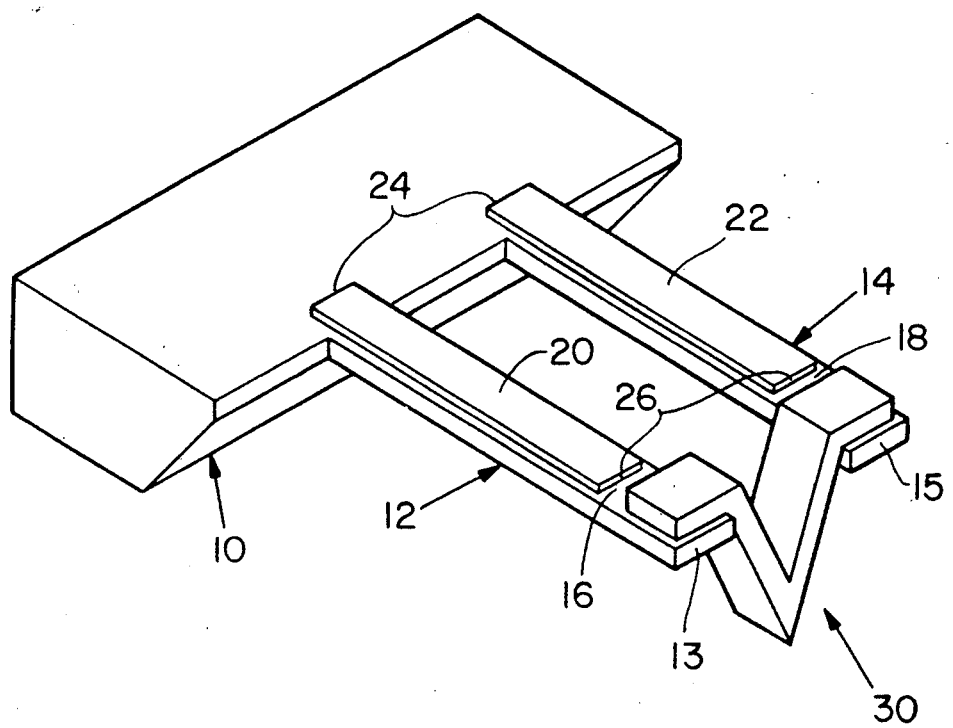
FIG. 1 is a perspective view of a preferred embodiment of a piezoelectric machine.

A preferred embodiment of a piezoelectric machine of the present invention is shown in FIG. 1. A silicon frame 10 and two cantilever beams 12 and 14, have been formed from a crystalline silicon wafer. A piezoelectric material such as zinc oxide (ZnO) has been secured to the top surfaces 16 and 18 of each beam 12 and 14 respectively. These ZnO films 20, 22 are positioned such that if they are caused to expand or contract in a direction along the length of the two beams 12 and 14, the beams will bend with the free ends 13 and 15 of the beams being lowered or raised from their initial undeflected positions.

Piezoelectric materials are known to undergo mechanical displacement when subjected to an electric field. By contacting the ends 24 and 26 of each piezoelectric film 20, 22 with suitable electric contacts, and applying a potential difference $V_o$ of sufficient magnitude across the length of each film, then the films 20, 22 will contract or expand depending upon the polarity of the applied field. A "V" shaped member or "foot" 30 is attached between the free ends of each beam 12, 14 by two extensions that meet a point. The foot 30 can be integrally made with the beams or mounted separately.

FIGS. 2a–2d illustrate a sequence of positions which the ends of the beams 12 and 14, and the attached foot 30, can assume upon the application of an appropriate electric signal across the films 20 and 22. FIG. 2a is an end view of the ends 13 and 15 of the two beams 20 and 22. The point 32 of foot 30 is aligned with the rest position R when the beams 20 and 22 are in the undeflected or normal position N. FIG. 2b shows that the ends 13 and 15 of the beams have been elevated above the undeflected position N while the point 32 of the foot 30 remains aligned with the rest position R. FIG. 2c shows the configuration of the point of the foot 30 to one side of R when the end 13 of beam 20 has been lifted above the height of the second beam 22. The ends 13 and 15 are then lowered as shown in FIG. 2d such that the point 32 contacts the plane S to one side of the rest position R. If the point 32 is in frictional contact with a surface in the plane S, then the return of both beams to the undeflected position N (as shown in FIG. 2a) from the position in FIG. 2d will result in a lateral force being applied to the surface by the foot or vice versa.

Thus by straightening the beams when the unit is in the position of FIG. 2d, the foot scrapes over the surface if the beams are restrained, or alternatively to move the unrestrained beams to a new position. This constitutes a walking motion.

A number of electromechanical characteristics of this system can be analyzed to illustrate the capabilities of the device shown in FIGS. 1 and 2. Consider first that the elevation of the tip of a single beam can be calculated to be $$\sigma = \frac{n\, d31 L^2\, V}{t^2}$$

where n = a numerical factor close to unity which depends on the exact geometry of the piezoelectric films, the thicknesses and stiffnesses of the substrate and the electrodes and whether the substrate is piezoelectric or not. For example, n=⅔ for a piezoelectric film of equal thickness and stiffness as a nonpiezoelectric substrate, while electrode dimensions are neglected. The quantity d31 is equal to the piezoelectric coefficient. L = the length of the cantilever beam, V = the voltage applied to the piezoelectric film, and t = the thickness of the piezoelectric film.

For a particular embodiment where the beam has a thickness of 1μ, a width of 10μ and a length of 200μ, the deflection is 0.2μ/V.

If any stiffness in the foot can be ignored, the length of the step s can be found using the expression:

$$s = \frac{2\,h\,\sigma}{a}$$

where h= the height of the beams above the surface and a = the distance between the beams. For the beam having the dimensions listed above, the stepsize would be about 0.6μ/V.

The force that can be exerted by a piezoelectric cantilever beam can be found to be:

$$F = \frac{3\,d31 E' t w V}{4L}$$

where E'= the effective Young's modulus of the beam and w = the width of the beam. For the beam having the dimension referenced above the force is about 2.5 nN/V.

The force F' the foot can exert when it is restrained is then $$F' = \frac{Fa}{h} = \frac{3ad31 E' t w V}{4hL}$$

Thus the force of the foot in the above example would be about 15 nN/V.

The associated spring constant k is F'/s:

$$k = \frac{3a^2 E' t^3 w}{8nh^2 L^3}$$

The mass m that can be lifted by the force is:

$$m = \frac{3d31 E' t w V}{4Lg}$$

where g g is the gravitational constant. For the beam referenced above the mass that can be lifted is 2.5 E=10 kg/V (the mass of a red blood cell is of the order of 5E=13 kg.)

The total stored mechanical energy available at the foot is then $$U = \tfrac{1}{2}ks^2 = \frac{3E' w n (d31)^2 L V^2}{4t}$$

For example, a cantilever beam with typical dimensions of 1μ×10μ×200μ has a mechanical energy content of 10−17 J/V .

This amounts to an energy density of 2.5×10−3 J/V m³, while a piezoelectric material like ZnO can support electric field strengths in excess of 10 V over a thickness of 1 μ, which gives a maximum energy density of 0.25 J/m³.

The conversion of electrical energy into mechanical energy by the piezoelectric effect is described by the square of the coupling factor, which for a material like ZnO is around 0.1, so the amount of applied electrical energy must therefore be of the order of 2.5 J/mhu 3.

The resonance frequency f of a cantilever beam can be written as $$f = \frac{.98t}{2\pi L^2}\, (E/p')$$

where p'= the effective specific density of the material. For the beam considered above the resonance frequency is about 32 kHz.

If we assume that the major components of the speed v with which a motor could operate would be the step size and the number of steps that can be taken per second, while we assume the latter to be equal to half of the resonance frequency of the first mode of the beam, we find:

$$v = \frac{.98 h n d31 V}{2at\pi}\, (E/p')$$

For example, maximum velocity of the motor at a given voltage is 1 cm/s(V).

An etched cantilever beam piezoelectric motor unit can be built in a number of ways. The beam can be formed, as illustrated in FIGS. 3A–3I, by first preparing the electrodes 92, 94 and the piezoelectric film 96 on the top surface of the beam, which is then still an integral part of a silicon wafer 88, and covering this by a protective succession of films (See FIG. 3A). In this layer of protective films a latent image is formed of the perimeter of the beam and of the bonding pads.

This latent image is formed by first depositing a SiN film 90 on the topside of the device followed by a SiO₂ film 98 which is deposited by LPCVD.

Figure 3A:
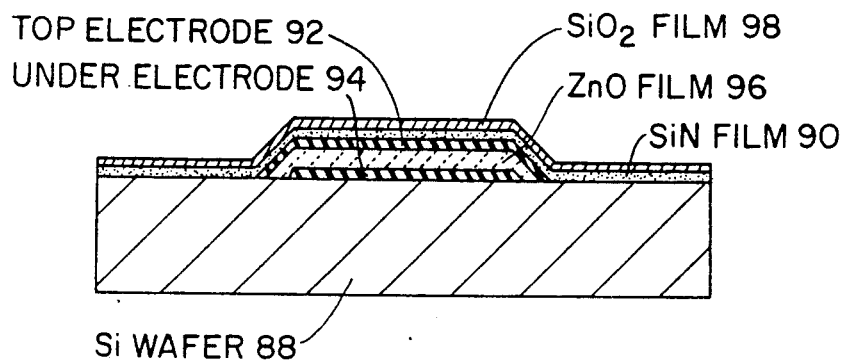
FIGS. 3A–3I illustrate a sequence of fabrication steps employed in the method of making the cantilevered beam of the present invention.
Figure 3B:
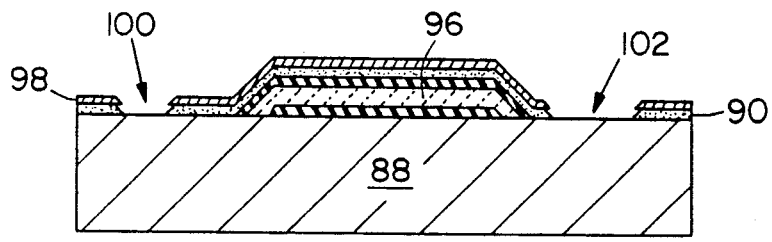

By means of a photolithographic process as shown in FIG. 3B, a window is etched in this SiO₂ film where the bonding pads 100 have to be uncovered and where the ditch 102 for the beam etch has to be formed. When the SiO₂ is etched, the resist is stripped and the SiN film is etched through the SiO₂ windows.

Figure 3C:
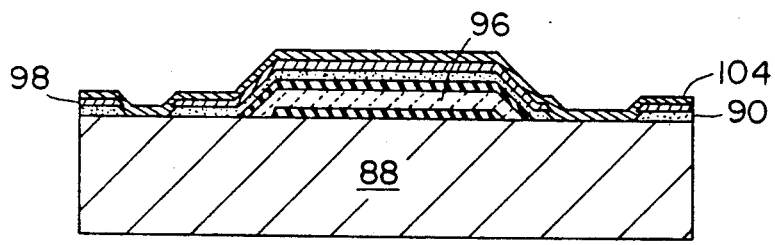
Figure 3D:
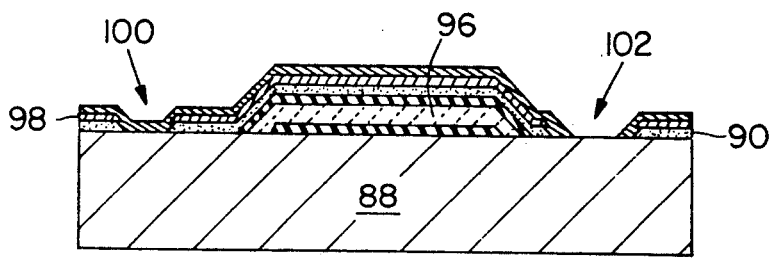
Figure 3E:
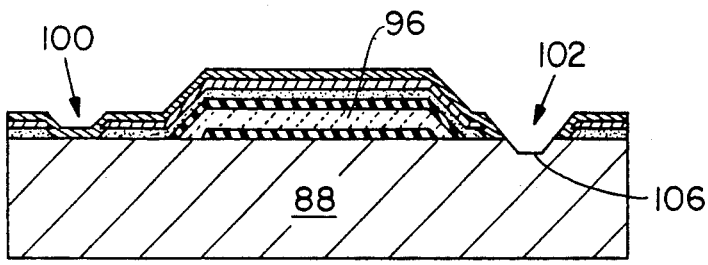

As seen in FIG. 3C, the top surface is now covered again with a SiO₂ film 104, on which a photolithography step is performed to open the window for the ditch 102 etch, but not for the bonding pads 100 (at FIG. 3D). The ditch is etched to the required depth 106 and thickness, as seen in FIG. 3E, which is monitored by observing the apex of the inverted pyramids arranged in a row, and with increasing sizes.

Figure 3F:
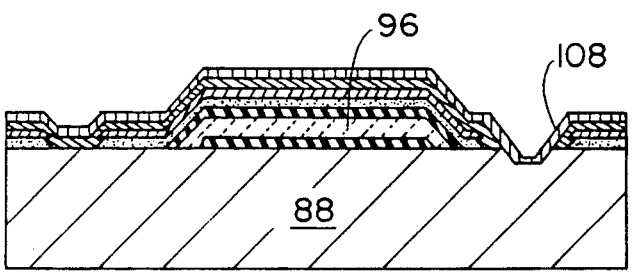
Figure 3G:
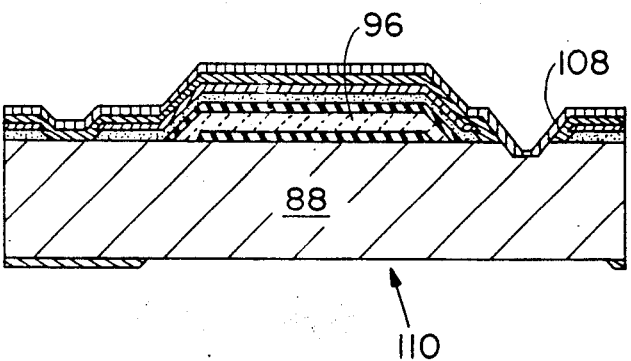
Figure 3H:
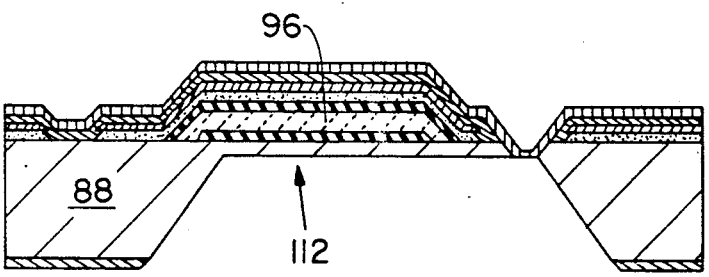

After the ditch has been etched, the front surface is again covered with a protective oxide 108 (at FIG. 3F). After this a window 110 is opened, as shown in FIG. 3G, from the backside of the wafer through which another anisotropic etching step takes place. This window must be large enough to give a bottom of the backside anisotropic well 112 to be of the size of the beam plus the ditch 106 around the perimeter. When the ditch 106 bottom is opened by the backside well etch, the etching of the well 112 is stopped and the beam formation is completed (at FIG. 3H).

The structure is now too fragile to be used in a regular photolithographic process, which is why the latent image of the future photolithography steps has already been stored.

Figure 3I:
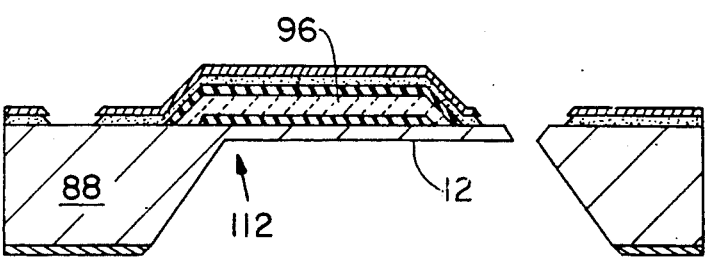

The detachment of the beam from its surrounding web and the opening of the windows for the bonding pads can be done by dipping the wafer in a series of successive etching baths. The next step is to etch the last three SiO₂ films from the top. This will at once free the beam and uncover the bonding pads, as shown in FIG. 3I.

This method avoids the use of a stopping layer of highly boron doped silicon. The beam thickness can now be controlled by mask dimensions rather than by diffusion depths. An advantage of this method is that a circuit can be formed in the beam because it is made of intrinsic silicon. Another advantage is that the beam thickness can be given any value, as we do not rely on a buried layer under an epitaxial layer.

For the formation of the beam with a foot, the process is changed by first making the beam as described above but without its piezoelectric film and electrodes.

Now a V groove can be etched between the beams and reoxidized. We then spin on resist and open a window in the resist across the groove.

This method can also be adjusted to make the foot as shown in FIG. 1 by first etching a "V" groove of a required depth between the legs, oxidize it, and later deposit polysilicon and form it in a strip which conforms to the profile of the "V" groove. The foot is detached in the same way as in the case of the etching of the cantilever beams, by etching from the backside. The etching stops at the oxide in the "V" groove. The oxide is removed at the same time as the webbing around the beam and the cover of the bonding pads are removed.

The foot can be made at the same time with the required depositions for a wheel with teeth, or gear, in such a way that the foot can drive the wheel.

Figure 4:
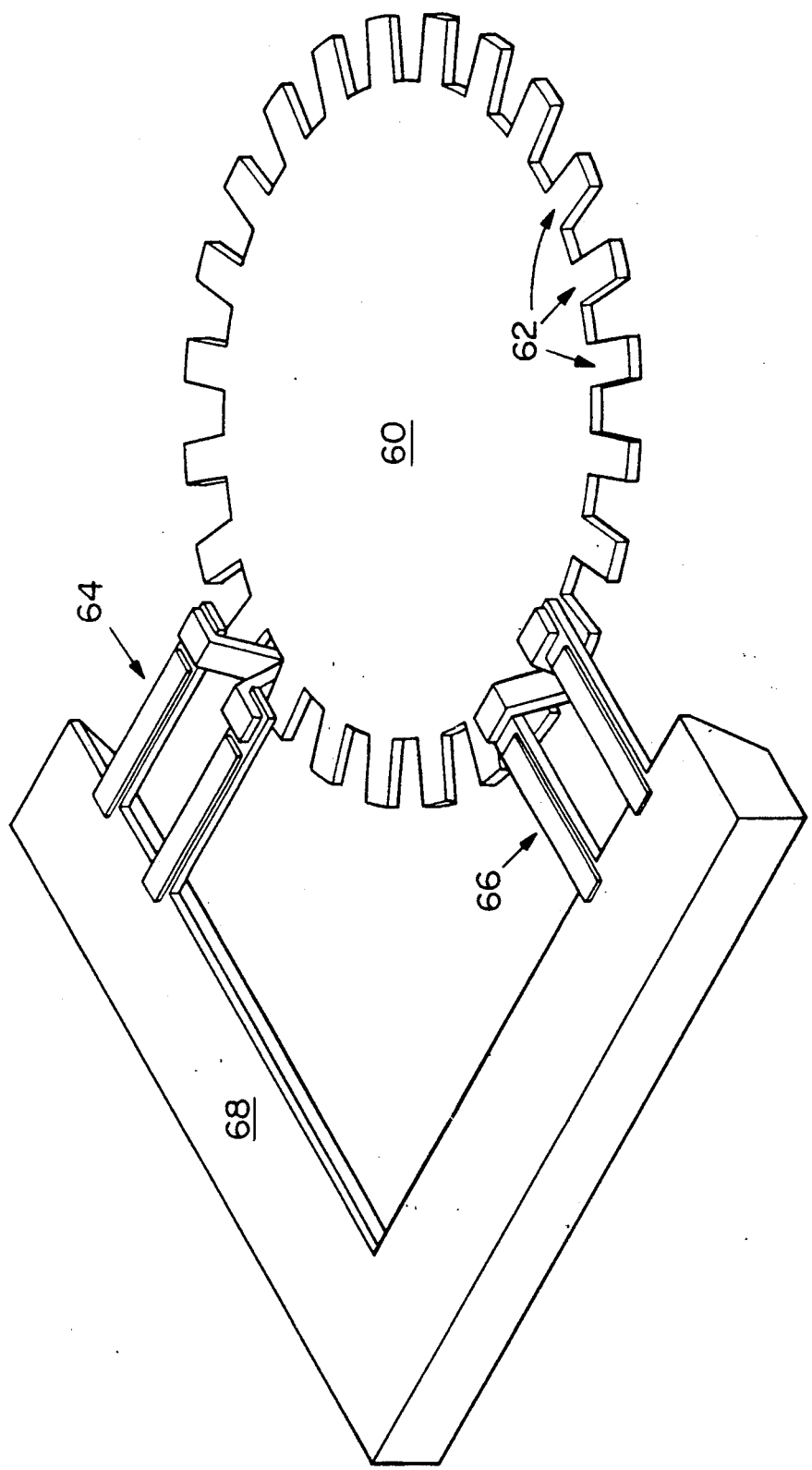
FIG. 4 is a perspective view of piezoelectric rotary drive unit.

FIG. 4 illustrates a rotary unit driven by two of the machines 64 and 66 of FIG. 1 that are mounted or integrally attached to a frame 68, and are operated in tandem to rotate a wheel 60. The feet of both machines mesh with teeth 62 located around the perimeter of wheel 60.

If the foot drives a wheel with indentations with radius r, as shown in FIG. 4, the angular velocity $\Omega$ of the wheel is $$\Omega = \frac{v}{2\pi r}$$

If a wheel is used with a radius equal to the length of the beam, the angular velocity $\Omega$ is approximately 8 revolutions per second.

Figure 5:
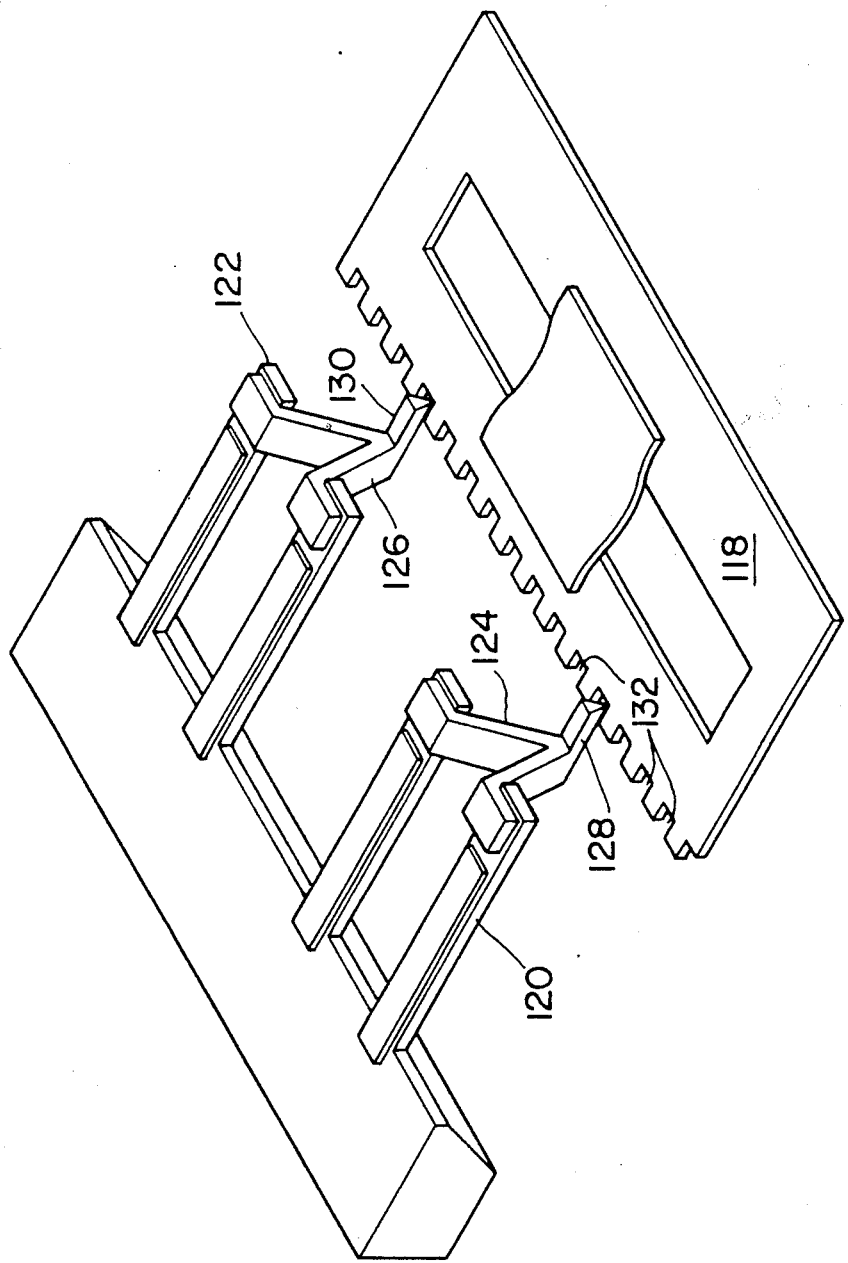
FIG. 5 is a perspective view of two motor units used to push a slider back and forth.

Alternatively, a polysilicon beam can be made by deposition of a strip of polysilicon over a thick oxide film, and later etching away the oxide from under the beam. The foot can be made an integral part of the beam. A groove can be etched into the oxide as the mold in which the foot can later be deposited. The total dimensions of the legs of a motor unit can now be much smaller, wherein a set of beams 200$\mu$ long and 1$\mu$ thick on which a piezoelectric film is deposited of equal thickness to the beams can now have step lengths of 0.2$\mu$ per applied volt. Taking into consideration that the maximum voltage over a 1$\mu$ thick piezoelectric film can easily be 10 V, this amounts to a step size of 2$\mu$. A slider 118 can be driven either by the foot directly or, as shown in FIG. 5, by two motor units 120 and 122 wherein the feet 124 and 126 of each unit are attached to a pair of levers 128 and 130 which engage notches 132 of the slider 118.

The polysilicon beam itself can be used as the bottom electrode and we can evaporate an aluminum film onto the piezoelectric to function as the top electrode.

The polysilicon beam should be anchored at the silicon substrate onto an area that has a doping concentration of the opposite sign as the rest of the wafer, to ensure that the beam and the foot are electrically isolated from the rest of the structure. This area could serve as an electrical ground.

Figure 6:
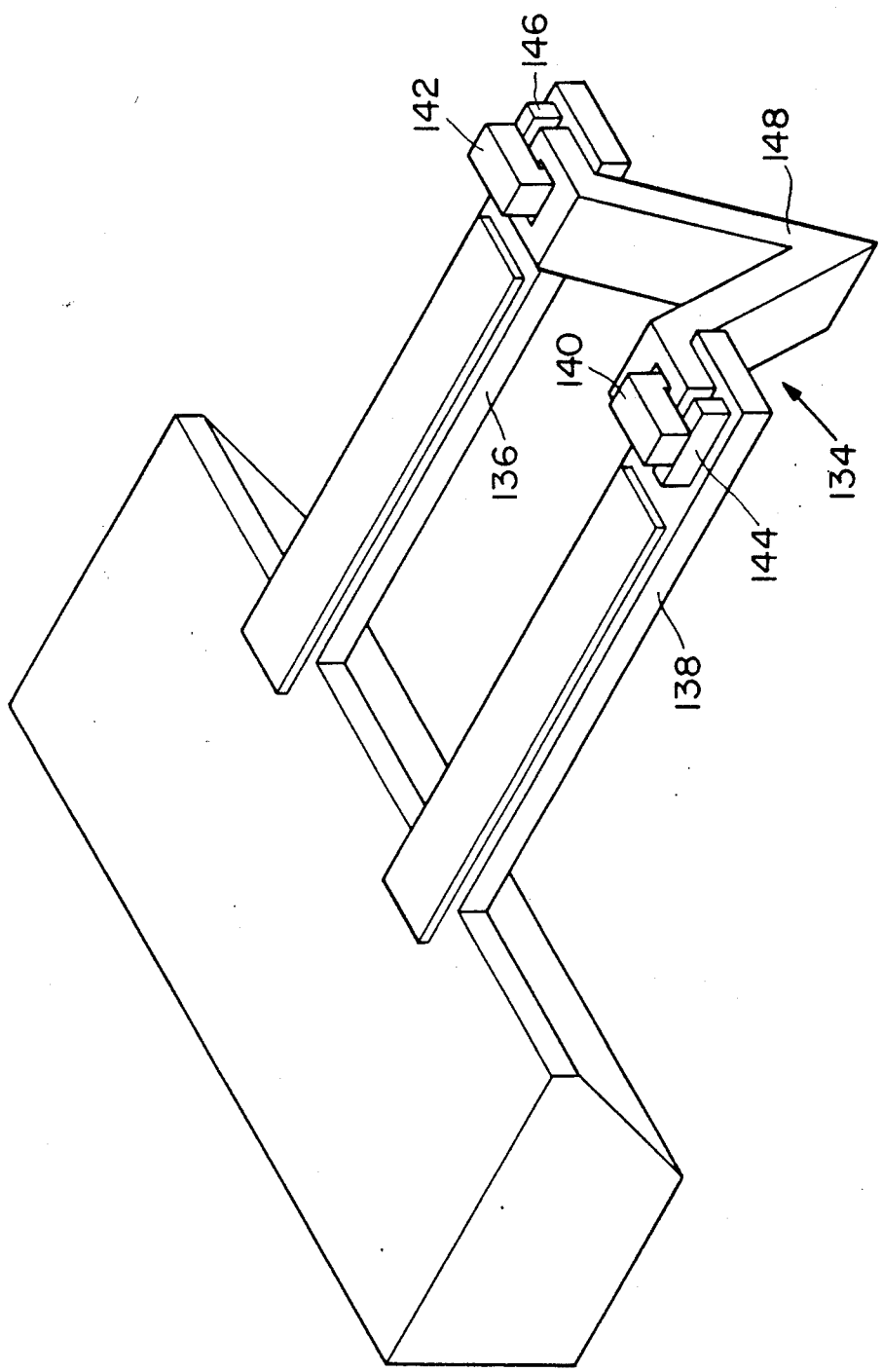
FIG. 6 is a perspective view of a hinged foot mechanism.

Similarly as described above a beam can be made of a strip of polysilicon, but now the foot is no longer an integral part of the beam any more. The foot is subjected to bending and torsion during its operation which results in an additional load on the cantilever beams. The efficient operation of the device can be improved if the foot can be attached to the beams by means of a hinge mechanism 134. A preferred embodiment of such a hinge is illustrated in FIG. 6. The hinge 134 provides for the securing of foot 148 to the beams 136 and 138 by means of mounts 144 and 146 and attachment arms 140 and 142 which extend through holes adjacent the two ends of the foot 148. This mechanism reduces the load on the beams during motor operation.

A polysilicon film is required for the formation of the beam, a second film is required for the formation of the foot, while a third film is required for the formation of the part of the hinge that is fastened to the beam and bridges a part of the foot. These films have to be separated by oxides or other suitable films with appropriate etching properties, such that the entire beam with hinging foot can be etched all at once, together with the removal of the cover of the bonding pads.

Figure 7:
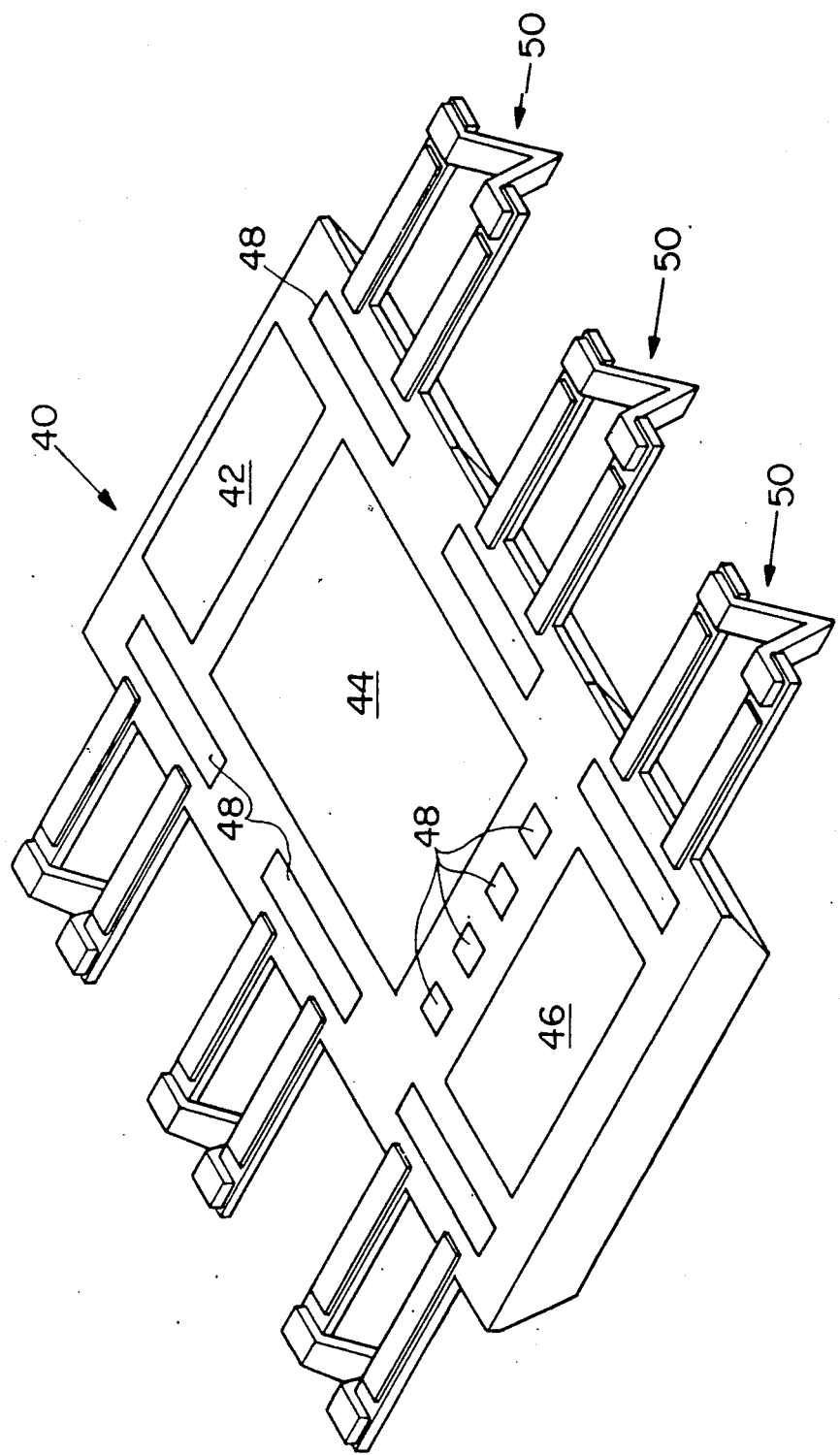
FIG. 7 is a perspective view of a micromechanical robot.

The walking motion of the machine in FIGS. 1 and 2 could be employed in a number of different applications. One such application is the embodiment shown in FIG. 7 where a plurality of the machines 30 shown in FIG. 1 are secured to a central platform 40 to provide the legs 50 of a robot. This robot can walk across a supporting surface.

The platform 40 contains a power source 44 that, in one preferred embodiment has one or more solar cells using light to power operation of the robot. A central processing circuit 46 is incorporated onto the platform so that specific functions can be programmed into the unit. A dc-dc converter 42 converts the signal from power source into a signal of appropriate current and voltage necessary to operate the local controls 48 associated with each leg 50.

Any number of systems can be used to communicate with the robot to either program its operation or directly control its motion. For example acoustic sensors 48 can be positioned on the platform 40 for this purpose.

Figure 8:
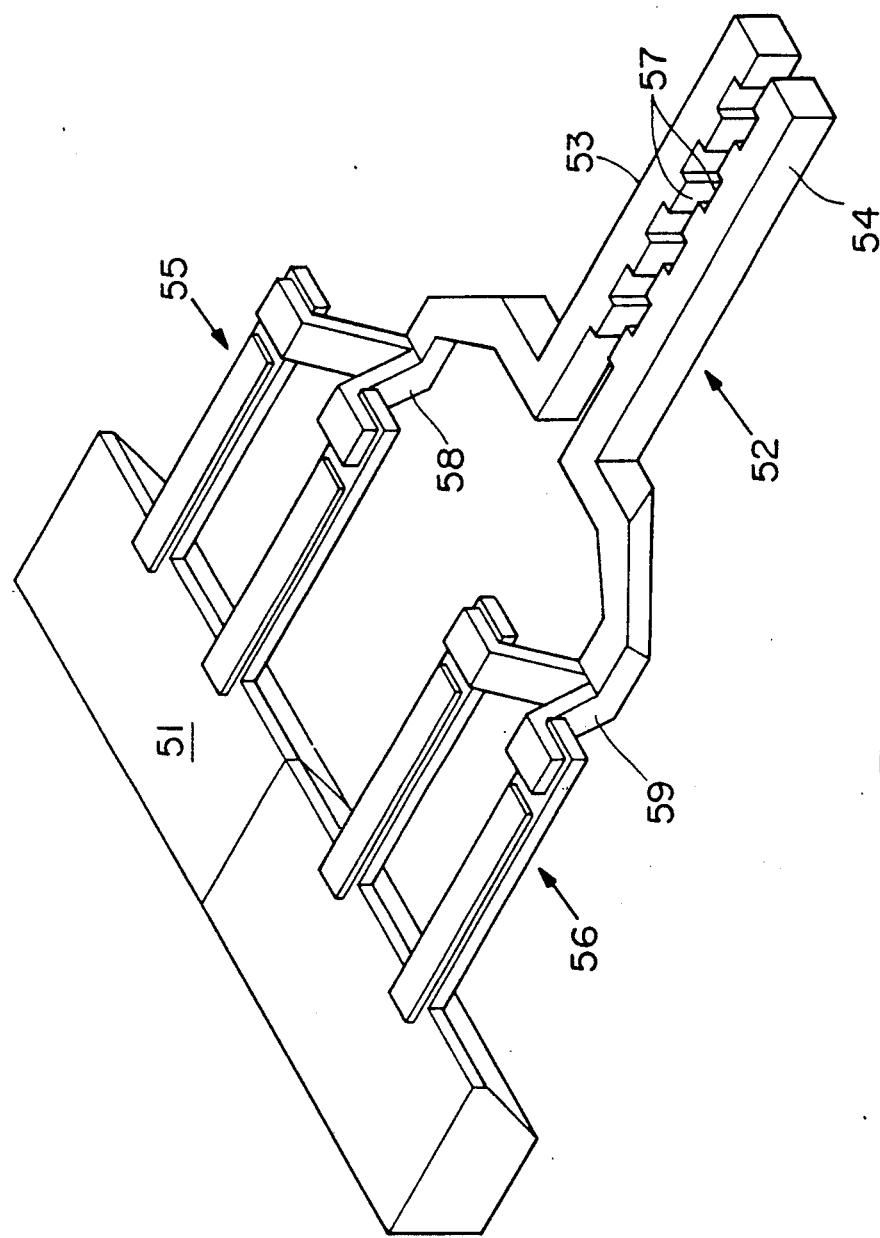
FIG. 8 is a perspective view of a unit used for grasping objects.
Figure 9:
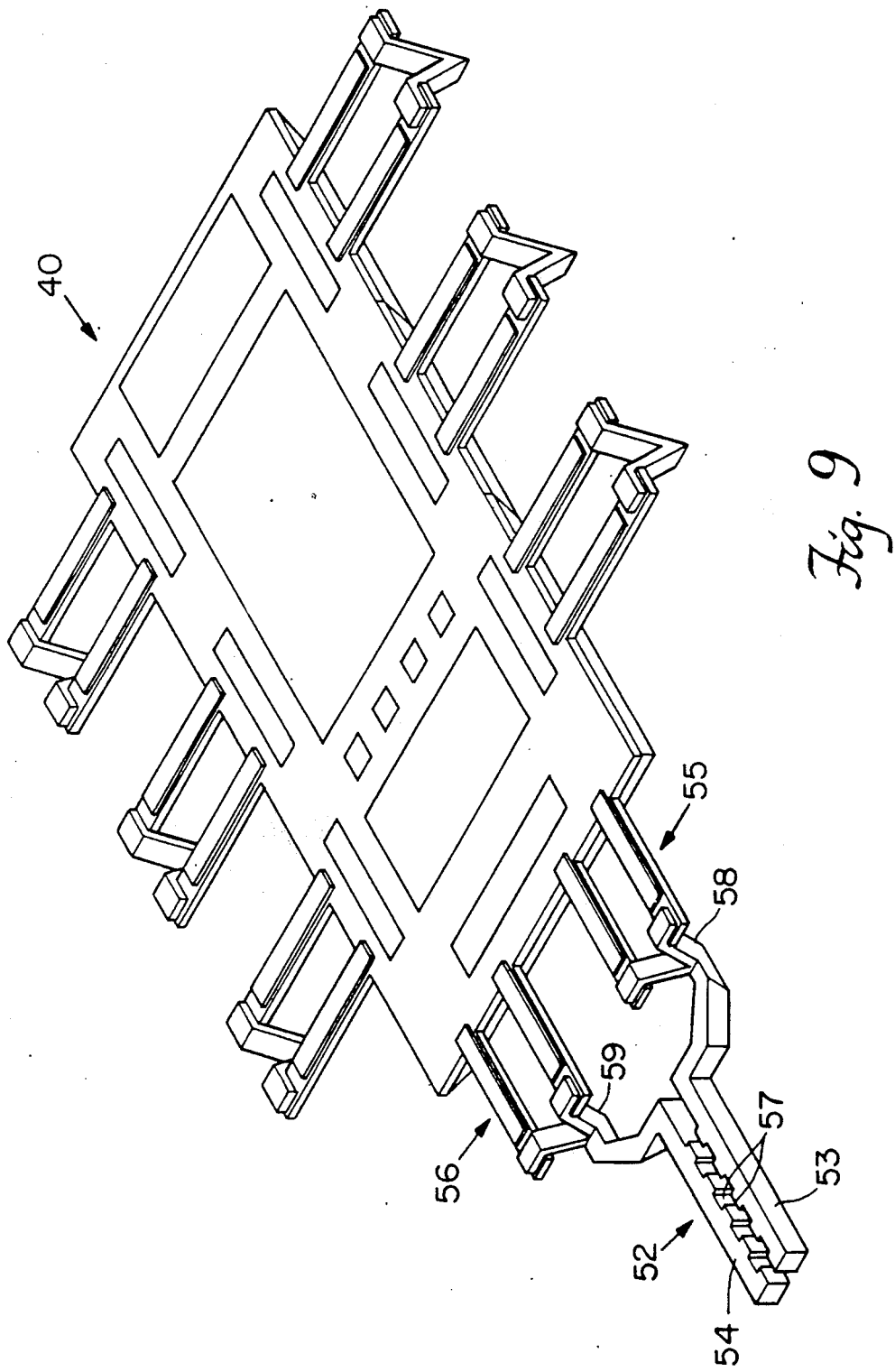
FIG. 9 illustrates the use of the unit shown in FIG. 8 with the robot shown in FIG. 7.

The robot can be provided with other types of piezoelectrically driven units much as the "jaws" 52 shown in FIG. 8 that could be used to grab and lift objects so that the robot could then transport them to another location. The jaws 52 are comprised of first and second elements 53 and 54 that are moved independently using the machine units 55 and 56. The two elements 53 and 54 have grabbing surfaces 57 that face each other, and which can be serrated as shown, or provided with some other frictional surface appropriate for a particular application. The elements 53 and 54 can be integrally made with the feet 58 and 59. Such an embodiment is shown in FIG. 9.

Figure 10:
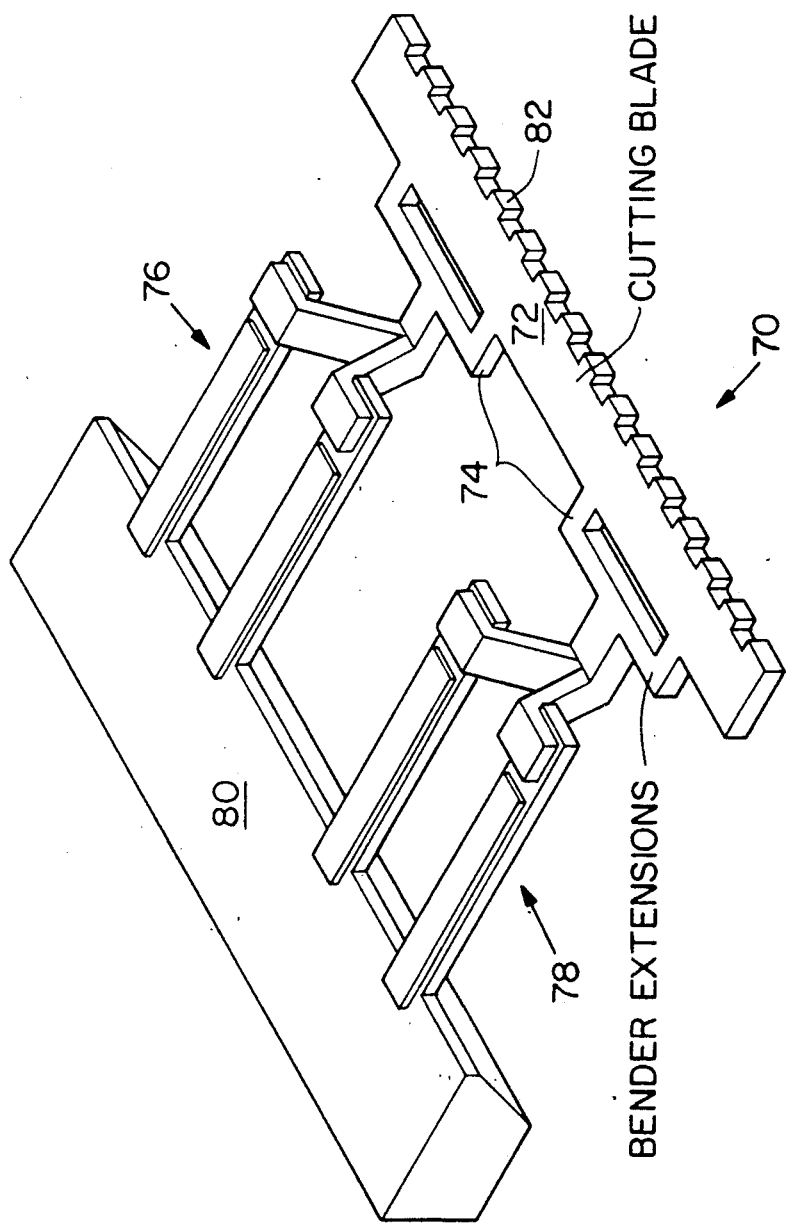
FIG. 10 is a perspective view illustrating the use of a cutting tool.

FIG. 10 illustrates a cutting tool 70 that can be used, for example, in microsurgical applications. Two sets 76 and 78 of the machine units shown FIG. 1 extend from the frame 80. A cutting blade 72 with serrated edge 82 is mounted to the units 76 and 78 by the bender extensions 74. By operating the units 76 and 78 in unison, the blade 72 can be made to reciprocate in a linear fashion to describe a cutting motion.

I claim:

1. A piezoelectric actuation machine for displacing rigid objects comprising:
   first and second cantilever beams extending from a frame, the beams comprising a piezoelectric material such that application of an electric potential across the material of each beam rotationally displaces the first and second beams relative to each other; and
   an actuating member secured between displaceable surfaces on the first and second beams and extending orthogonally from a plane through the beams such that relative displacement of the first and second beams displaces a portion of the member in a direction orthogonal to beam displacement and translates a rigid object contacting the displaced portion of the member relative to the member and the frame.

2. The piezoelectric machine in claim 1 wherein the first and second beams are parallel in a undisplaced position.

3. The piezoelectric machine of claim 1 wherein said member is hingably attached to each beam.

4. The piezoelectric machine of claim 1 wherein said member has a rest position and a plurality of displaced positions in the orthogonal direction.

5. The piezoelectric machine of claim 1 wherein said member comprises first and second extensions, the extensions being joined at one end extending out of the plane through the beams, the first extension being secured to the first beam and the second extension being secured to the second beam.

6. The piezoelectric machine of claim 4 wherein said member drives a wheel.

7. The piezoelectric machine of claim 4 wherein said first and second beams are comprised of silicon.

8. The piezoelectric machine of claim 1 further comprising third and fourth piezoelectrically driven beams, a first gripping member secured to the actuating member and a second gripping member secured to a second actuating member between the third and fourth beams such that the gripping members can be brought together and separated to grasp and release objects.

9. The piezoelectric machine of claim 1 further comprising a cutting surface mounted on the actuating members such that movement of the first and second beams displaces the cutting surface to cut objects.

10. A piezoelectric machine comprising a plurality of piezoelectrically driven members that support the machine that is positioned on a support surface such that correlated movement of the members displaces the machine relative to the support surface, each piezoelectrically driven member comprising a first beam secured to the machine and having a piezoelectric material covering a surface of the first beam, and a second beam secured to the machine and having a piezoelectric material covering a surface of the second beam.

11. The piezoelectric machine of claim 10 further comprising a power sources on the machine for providing an electric potential to the piezoelectrically driven members.

12. The piezoelectric machine of claim 11 further comprising a control circuit for controlling the application of the electric potential to each member.

13. The piezoelectric machine of claim 10 further comprising a memory for recording a sequence of movements for the members.

14. The piezoelectric machine of claim 10 further comprising a transducer to transmit a signal to the machine from an external source.

15. The piezoelectric machine of claim 10 further comprising a coupling member secured to a displaceable surface of each beam and having a frictional surface to frictionally engage the support surface.

16. The piezoelectric machine of claim 10 further comprising a gripping device secured to the machine to grasp and transport objects.

17. The piezoelectric machine of claim 10 further comprising a cutting device secured to the machine to cut objects.

18. A piezoelectric micromachine comprising:
   a support frame from which a flexible semiconductor structure extends;
   a rigid object in contact with the flexible structure; and
   a piezoelectric material secured to the semiconductor structure such that application of an electric field across the material causes a displacement of the flexible structure to actuate movement of the object relative to the frame.

19. A piezoelectrically driven member comprising:

a silicon support frame having a silicon member with one end integral with the frame and a second end displaceable relative to the frame;

piezoelectric material secured to a surface of the silicon member such that an expansion or contraction of the material displaces the second end of the member;

a rigid body to be contacted by the displaceable end of the member; and an electrical contact grid formed adjacent to the piezoelectric material to provide an electric potential across the material such that the application of an electric potential displaces the rigid body contacting the silicon member relative to the frame.

20. The piezoelectrically driven member of claim 19 further comprising at least one additional piezoelectrically driven silicon member formed adjacent the first member.

21. The piezoelectric micromachine of claim 18 wherein the semiconductor material is integrally formed with the support frame.

22. The piezoelectric micromachine of claim 18 wherein the object comprises a support surface such that actuated movement of the semiconductor structure translates the machine across the support surface.

23. The piezoelectric micromachine of claim 18 further comprising a plurality of flexible semiconductor structures extending from the frame having a piezoelectric material secured thereto.

24. The piezoelectric micromachine of claim 23 further comprising a member secured to displaceable portion of two of the structures.

25. The piezoelectric micromachine of claim 24 wherein said member contacts the rigid body to be actuated.

26. The piezoelectric micromachine of claim 18 wherein the semiconductor structure further comprises an electrical circuit.

27. The piezoelectrically driven member of claim 19 further comprising a control circuit in conductive contact with the piezoelectric material to control displacement of the silicon member relative to the frame.

28. The piezoelectrically driven member of claim 19 wherein the rigid body is unattached to the silicon member.

29. The piezoelectrically driven member of claim 19 further comprising a second piezoelectrically driven silicon member and a coupling member such that the displaceable ends of the silicon members are coupled by the coupling member.

30. A piezoelectrically driven machine comprising:

a semiconductor member having a plurality of flexible piezoelectrically driven arms that support the member relative to a support surface; and a control circuit on the semiconductor member to control the application of an electric field to each of the piezoelectrically driven arms to produce correlated movement of the arms such that the semiconductor member is displaced relative to the support surface by the arms.

31. The machine of claim 30 further comprising a power source on the semiconductor member.

32. The machine of claim 30 further comprising a memory on the semiconductor member.

33. The machine of claim 32 further comprising a transducer for programming the memory.

34. The machine of claim 30 wherein each arm comprises first and second bimorphs.

35. The machine of claim 30 wherein the arms are integrally formed with the member.

36. The machine of claim 35 wherein at least a portion of the circuit is formed on or the arms.

* * * * *